US008149416B2

(12) United States Patent
Akcakir

(10) Patent No.: US 8,149,416 B2
(45) Date of Patent: Apr. 3, 2012

(54) APPARATUS AND METHOD FOR DYNAMIC CELLULAR PROBING AND DIAGNOSTICS USING HOLOGRAPHIC OPTICAL FORCING ARRAY

(75) Inventor: Osman Akcakir, Oak Lawn, IL (US)

(73) Assignee: Arryx, Inc., Chicago, IL (US)

( * ) Notice: Subject to any disclaimer, the term of this patent is extended or adjusted under 35 U.S.C. 154(b) by 368 days.

(21) Appl. No.: 12/289,589

(22) Filed: Oct. 30, 2008

(65) Prior Publication Data

US 2009/0128825 A1    May 21, 2009

Related U.S. Application Data

(63) Continuation-in-part of application No. 11/581,516, filed on Oct. 17, 2006, now Pat. No. 7,460,240.

(60) Provisional application No. 60/726,620, filed on Oct. 17, 2005, provisional application No. 61/071,456, filed on Apr. 30, 2008.

(51) Int. Cl.
*G01B 9/021* (2006.01)
(52) U.S. Cl. ...................................................... 356/457
(58) Field of Classification Search .......... 356/457–458, 356/502–503, 512, 515
See application file for complete search history.

(56) References Cited

U.S. PATENT DOCUMENTS

| | | | |
|---|---|---|---|
| 5,689,109 A | 11/1997 | Schutze | |
| 6,055,106 A | 4/2000 | Grier et al. | |
| 6,416,190 B1 | 7/2002 | Grier et al. | |
| 6,833,923 B2 * | 12/2004 | Florin et al. | 356/601 |
| 7,460,240 B2 * | 12/2008 | Akcakir | 356/457 |
| 7,473,890 B2 * | 1/2009 | Grier et al. | 250/251 |
| 7,839,551 B2 * | 11/2010 | Lee et al. | 359/15 |
| 7,948,632 B2 * | 5/2011 | Gustafsson et al. | 356/458 |
| 2004/0085540 A1 | 5/2004 | Lapotko et al. | |

(Continued)

FOREIGN PATENT DOCUMENTS

JP    2003-506711 A    2/2003
(Continued)

OTHER PUBLICATIONS

Gittes, Frederick et al. "Interference model for back-focal-plane displacement detection in optical tweezers". Optics Letters, vol. 23, No. 1, Jan. 1, 1998, pp. 7-9.*

(Continued)

*Primary Examiner* — Michael A Lyons
(74) *Attorney, Agent, or Firm* — Jean C. Edwards, Esq.; Edwards Neils PLLC

(57) ABSTRACT

The present invention utilizes a holographic optical forcing array for dynamic cellular probing and diagnostics. A holographic optical trapping system generates optical forces on objects so that deformations thereof may be quantified. In one embodiment, digital holography is used to generate an interference pattern, and an analysis thereof determines the phase profile which yields a measurement of the objects' shape deformation using only one image. In another embodiment, phase-stepped holography allows the phase profile of an object to be measured using only one image, by using a holographic optical element to make phase-shifted replicas of the beam in space. In another embodiment, the optical forcing array applies optical forces to beads placed on the objects' surface, deforming the objects. The beads' position is determined by applying Mie theory, and analysis thereof yields the three dimensional position of the beads, and a measurement of the deformation displacement on the objects' surface.

86 Claims, 7 Drawing Sheets

U.S. PATENT DOCUMENTS

| | | |
|---|---|---|
| 2005/0196552 A1 | 9/2005 | Lehmann et al. |
| 2007/0086919 A1 | 4/2007 | Akcakir |
| 2007/0182962 A1 | 8/2007 | Bearman et al. |

FOREIGN PATENT DOCUMENTS

| | | |
|---|---|---|
| JP | 2003-121749 A | 4/2003 |
| JP | 2004-527255 A | 9/2004 |
| WO | WO-2001-011340 A1 | 2/2001 |
| WO | WO-2002-088704 | 11/2002 |
| WO | WO-2004-065923 A1 | 8/2004 |

OTHER PUBLICATIONS

Guck, J., et al., "Optical Deformability as an Inherent Cell Marker for Testing Malignant Transformation and Metastatic Competence", Biophysical Journal, 88:3689-98, 2005.

Guck, J., et al., "The Optical Stretcher: A Novel Laser Tool to Micromanipulate Cells", Biophysical Journal, 2001, 81:767-84.

Lekka, M., et al., "Elasticity of normal and cancerous human bladder cells studied by scanning force microscopy", European Biophysics Journal, 1999, 28:312-6.

Popescu, G., et al., "Fourier phase microscopy for investigation of biological structures and dynamics", Optics Letters, 2004, 29(21):2503-5.

Dufresne, E.R., et al. "Computer-Generated Holographic Optical Tweezers Arrays", Dept. of Physics et al., Oct. 27, 2000, 8.

Janmey, P.A., et al. "Viscoelastic Properties of Vimentin Compared with Other Filamentous Biopolymer Networks", The Journal of Cell Biology, 1991, 113(1), 155-160.

Jenmey, P.A., et al. "Dealing with mechanics: mechanisms of force transduction in cells", Trends in Biochemical Sciences, 2004, 29(7), 364-370.

Voros, Janos, "The Density and Refractive Index of Adsorbing Protein Layers", Biophysical Journal, 2004, 87, 553-561.

Kang, Y., et al. Epithelial-Mesenchymal Transitions: Twist in Development and Metastasis, Cell, 2004, 118, 277-279.

Thiery, Jean Paul, Epithelial-Mesenchymal Transitions in Tumour Progression, Nature Publishing Group, 2002, 2, 442-454.

Ghosh, S., et al. "Loss of Adhesion-Regulated Proteinase Production is Correlated with Invasive . . . Cell Carcinoma", American Cancer Society, 2002, 2524-2533.

Yang, J., et al. "Twist, a Master Regulator of Morphogenesis, Plays an Essential Role in Tumor Metastasis", Cell, 2004, 117, 927-939.

Paszek, M.J., et al. "The Tension Mounts: Mechanics Meets Morphogenesis and Malignancy", Journal of Mammary Gland Biology and neoplasia, 2004, 9(4), 325-342.

MacKintosh, F.C., et al. "Elasticity of Semiflexible Biopolymer Networks", Physical Review Letters, 1995, 75(24), 4425-4429.

Popescu, G., et al. "Motility of Live Cancer Cells Quantified by Fourier Phase Microscopy", SPIE-OSA, 2005, vol. 5864, 58640A-1.

\* cited by examiner

APPARATUS AND METHOD FOR DYNAMIC CELLULAR PROBING AND DIAGNOSTICS USING HOLOGRAPHIC OPTICAL FORCING ARRAY

The present application is a continuation-in-part of U.S. patent application Ser. No. 11/581,516, filed Oct. 17, 2006, now U.S. Pat. No. 7,460,240 which claims priority from U.S. Provisional Patent Application No. 60/726,620, filed Oct. 17, 2005, and also claims priority from U.S. Provisional Patent Application No. 61/071,456, filed Apr. 30, 2008, the contents of all of which are herein incorporated by reference in their entirety.

BACKGROUND OF THE INVENTION

Diseases are often characterized by their unique molecular and/or genetic fingerprints. However, for many diseases, including cancer, this has yielded limited success; partly because there are many possible ways the molecular pathways in a cell may become pathological, there is much to learn.

Cancer is still a leading killer in the United States, despite decades of focused research activity on the problem. However cells, aside from being biochemical and genetic entities, are also mechanical entities which have physical properties such as elasticity. Diseases which effect the cytoskeletal protein network of cells (i.e. the structural integrity of the cell), including cancer, should naturally yield cells with altered mechanical properties (e.g. elasticity). This area of research is in still in its infancy, but recent research has successfully been able to distinguish cancerous cells from normal ones based on experimentally measuring an effective cellular elasticity (see ref. Guck et al., ref. Cross, S. E., Yu-sheng, J., Rao, J., Gimzewski, J. K., "Nanomechanical analysis of cells from cancer patients", Nature Nanotechnology, vol. 2 (2007) p. 780-783) by optical means.

Existing techniques to measure the elastic properties of cells suffer from two main difficulties: 1) the technique is exceeding slow, making it difficult to envision translating into the clinical world, and 2) it is difficult to avoid mechanical contact with the sample, and so probe needle contamination is a real danger when measuring a series of cells.

Accordingly, a technique which can measure cells on a surface, which avoids damage to the cell, and which can speed up the technique to make it commercially viable, is needed.

SUMMARY OF THE INVENTION

One object of the present invention is to determine the deformation of cells using a holographic optical forcing array for dynamic cellular probing and diagnostics, using an adaptation of a digital holographic apparatus, or a holographic phase-stepped apparatus. The apparatus allows optical forces to be applied to adherent cells, and for the resultant surface deflections to be determined by a sensitive and quantifiable measurement.

The spatially modulated optical force microscope (SMOFM) of the present invention will allow quantification of the deflections of the cell surface due to optically applied surface forces, to be detected with interferometric sensitivity (sub-nanometer sensitivity). Alternatively, SMOFM can be used to quantify the deflections of the cell surface due to non-optically applied surface forces (i.e., hydrodynamic, hydrostatic, electrostatic, magnetic, osmotic, mechanical, or inertial forces). The quantification is performed by imaging a sequence of four (4) phase shifted replicas of the image using a computer-controlled spatial light modulator, and calculating the pixel by pixel optical path-length using existing algorithms. The change in optical path lengths, and consequently shape changes, may be determined (assuming the refractive indices of each component fraction does not change).

Spatial Light Modulation of light is involved in up to two different ways in this invention. First, it is used in the detection of the path-length changes in the sample by spatially modulating the Fourier transform of the sample image that is illuminated with low-coherence light in transmission (imaging). Second, a separate spatial light modulator may be used to sculpt the laser light used for optically forcing object(s) in user-defined positions with user-defined intensities in the field of view (optical forcing). Each spatial light modulator in this embodiment modulates the light signal from a different source (Spatial Light Modulator (SLM) SLM1: imaging source, i.e. low-coherence diode), Spatial Light Modulator (SLM) SLM2: laser source for optical forcing).

Thus, with the present invention, optical deformability of any type of cell may be measured on the spatially modulated optical force microscope (SMOFM), so that diseased cells, including cancer cells, that have a unique optical deformability signature may be identified. In addition to being used as a diagnostic tool, the spatial light modulated force microscope may also be used as an investigative tool to understand the causes of any change in optical deformability due to a particular diseased cell state. Optical deformability of such cells may be correlated with structural protein expression levels and patterns, for example, allowing the spatially modulated force microscope to uncover the molecular origins for the changes in the viscoelastic responses of cells brought on by disease.

The apparatus of the present invention is optically based, so it has the advantages of being a quick and sterile measurement platform. In contrast to the prior art, the objects or cells to be probed in the present invention may be adhering to a surface (i.e., microscope cover slip surface), and so are able to retain their naturally present focal adhesions and stress fibers.

The present detection technique (using spatially modulated optical microscopy) is a much more sensitive technique for the detection of deformation, with sub-nanometer level sensitivity, compared to that of prior art methods. The greater sensitivity of the present invention has two important advantages: 1) a greater dynamic range of elastic responses may be probed, and 2) detectable deformations may be achieved at lower laser powers. The second advantage is an important consideration for parallelization.

In another embodiment, the optical deformability of the normal and diseased cells may be measured and correlated with measurements of cytoskeletal/structural protein expression. Protein expression may be determined by fluorescently tagging the targeted protein, and collecting fluorescence images for example.

In this way the optical force microscopy apparatus of the present invention is a valuable tool for correlating molecular and genetic patterns in cells with a mechanical measurement of deformability, adding a new dimension to the characterization of cancerous phenotypes. The present invention also provides a basis for a cancer screening assay based on a deformability measurement parameter.

In another embodiment consistent with the present invention, a novel adaptation of digital holography is used to detect the optical deformability of objects or cells. In this embodiment, the reference beam is mutually coherent with the object beam, so that an interference pattern is generated at a detector, and the object beam and reference beam are combined in an off-axis geometry at the detector. With the analysis of the interference pattern at the detector, the deformation in shape of the objects or cells can be calculated and determined from a quantitative measurement of the phase profile. Accordingly, the quantitative phase profile of the objects or cells may be obtained from the interference pattern of the images of the objects or cells at the detector using standard techniques. Thus, in this embodiment, the phase is not controlled as in the previous Fourier phase method, however the phase profile may be numerically reconstructed from a single image by using calculational methods as outlined herein.

In yet another embodiment consistent with the present invention, and based on the same principles as in the previous Fourier Phase embodiment, a modified technique for quantitatively measuring the optical path length as opposed to using the above-identified Fourier Phase technique, is a method called phase-stepped holography, which allows the phase profile of an object or cell to be measured using only one image. In holographic phase-stepped interferometry, a mutually coherent reference beam and an object beam interfere, generating an interference pattern is at the detector. However, in this embodiment, a holographic optical element and transfer lens, are inserted between the object beam and a beam splitter, and which diffracts the beam into several beamlets after passing through the sample, and before being directed by the beam splitter into the detector. The holographic optical element splits the beam and makes replicas of the beam in space (i.e., phase-stepping the image in space)—in contradistinction to phase shifts in time, as is performed in the Fourier phase microscopy component of the technique disclosed above. Thus, the phase-delayed or phase-stepped replicas of the image of the objects are diffracted into four quadrants of the detector, and simultaneously interfered with the reference beam. A computer computes the phase profile of the objects from the four holographically phase-stepped replica images interfered with the reference beam. Thus, this embodiment provides the advantage that only one image is used to capture all four phase shifted images, and thus allowing the phase profile of an object to be measured using only one image—which provides greater speed and efficiency. The measurement of the phase profile and the optical path lengths is the same as discussed above in the Fourier phase microscopy method.

In yet another embodiment, a modified technique for quantitatively measuring the optical path length changes upon application of the optical forces is presented. This embodiment utilizes beads (e.g., micron diameter silica beads) placed on the surface of the cell(s)/object(s) to be probed. The optical forcing array applies optical forces to these beads thereby deforming the underlying cell(s)/object(s). The beads' position may be determined by applying Mie theory to the in-line holographic images of the beads, which are interference patterns between the wave diffracted by the bead and the undiffracted wave. The imaging laser is used in transmission-mode and is the source that generates the holographic images on the detector (in-line holography). Analysis of the interference fringes by Mie theory yields the three dimensional position of the bead (among other variables). By comparing the z position (z direction parallel to optic axis) of the beads before and after the optical trap is applied to the bead, a measurement of the deformation displacement on the surface of the cell/object. This displacement, in addition to the knowledge of the trap power/optical trapping force and an estimate of the contact area between the bead and cell/object allows a measurement of the elastic modulus (e.g., Young's modulus). A background image may also be taken, for correction purposes without the bead, which takes into account the scattering due to the cell(s)/object(s) alone.

Thus, the various embodiments of the present invention allows optical forces to be applied to objects, for example, and their resultant surface deflections to be sensitively and quantifiably measured. The present invention allows quantification of the deflections of the cell surface due to optically applied surface forces, to be detected with interferometric sensitivity (sub-nanometer sensitivity). The change in optical path lengths or quantitative changes in the shape of the cells, may be determined, so that diseased cells, including cancer cells, that have a unique optical deformability signature may be identified.

Thus, the present invention is a valuable tool for correlating molecular and genetic patterns in cells which show a mechanical measurement of deformability, adding a new dimension to the characterization of cancerous phenotypes. The present invention also provides a basis for a cancer screening assay based on a deformability measurement parameter.

There has thus been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

Figure 1:
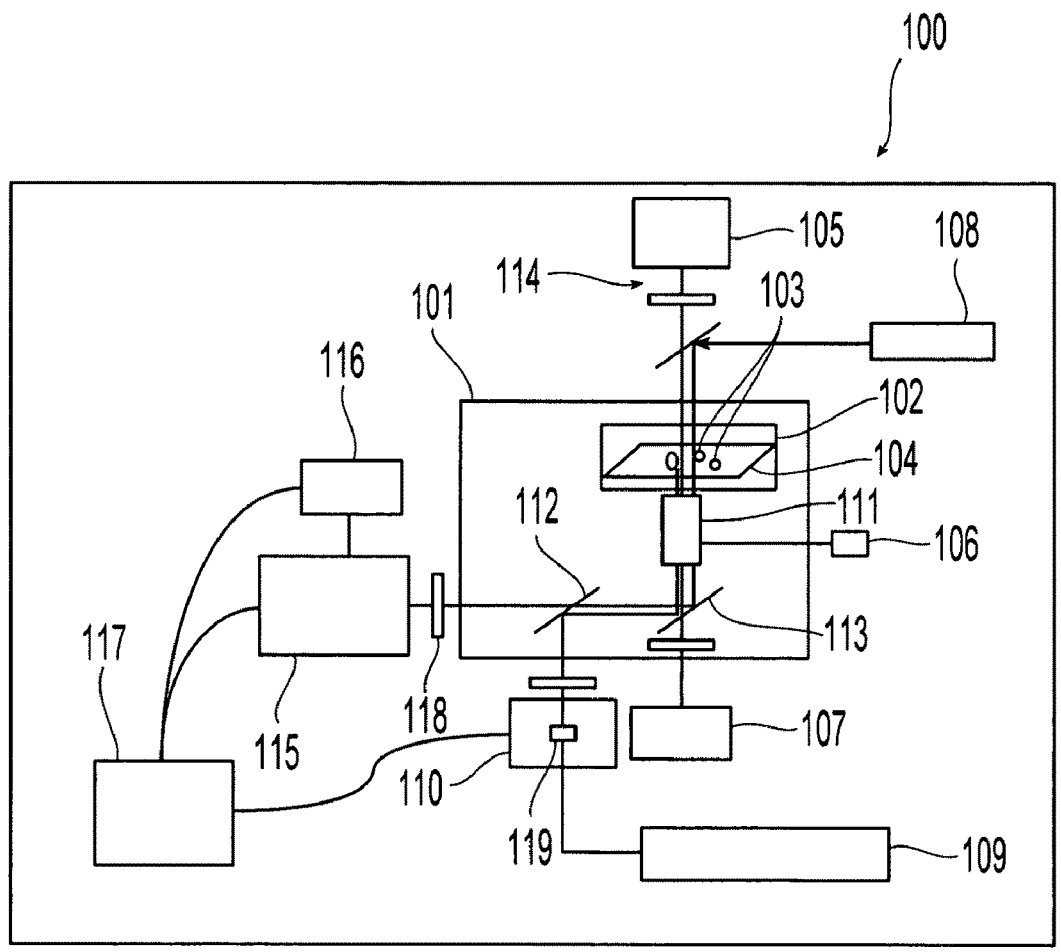
FIG. 1 shows an optical force measurement apparatus according to one embodiment consistent with the present invention.

The present invention is related to an optical force measurement device that can apply optically based forces and sensitively detect the resulting deformations in objects, such as cells, while the objects rest on or adhere to a surface, rather than being in suspension as in previous applications.

In particular, in one embodiment, the present invention measures deformations in the object as a function of an applied optical force, using holographic optical trapping technology, for example, to direct optical forces to potentially many regions of interest simultaneously.

In another embodiment, the present invention measures deformations in the object using a quantitative phase contrast microscopy technique—e.g. spatially modulated optical force microscopy (SMOFM).

In a preferred embodiment, the present invention utilizes spatially modulated optical force microscopy (SMOFM) with single beam optical force probing capability or with a holographic optical trapping system capable of multi-beam optical force probing coupled to a microscope objective, to generate a probe beam(s) as a force probe to perturb the object that is adhered or resting on a surface, so that deformations of the object(s) may subsequently be measured.

In another embodiment, a single beam optical force probe may be applied without a spatial modulating component (i.e., an SLM). This beam may be directed to cell(s)/object(s) of interest via movable mirrors, acousto-optic modulator (AOM) or other suitable devices.

The present invention allows optically forced objects to be measured without being in suspension, in contrast to prior art techniques. In fact, the object being measured in the present invention, may be any type of adherent cell, and optical techniques are used to determine whether the cell is a normal or a cancerous cell. Other cell types (e.g., stem cells) or cell states (e.g., disease states) may also be detected and/or characterized by optical deformability provided that the target cell type or cell state has a characteristic elastic or viscoelastic response to the optically based force probe.

The optically generated surface forces that generate the cellular deflections of interest is due to the conservation of photon momentum as it traverses media of different refractive indices. When a photon in media 1 with refractive index $n_1$ crosses over into media 2 with refractive index $n_2$, the photon's momentum changes from $n_1 E/c$ to $n_2(1-R)E/c$, where E is the photon energy and R is the reflectivity given by the Fresnel formulas (e.g., $R \sim 10^{-3}$). In addition there is a reflected component whose photon momentum is $n_1 RE/c$. For momentum conservation a momentum on the surface is picked up, given by $\Delta p$.

The surface thus, experiences a force $F = \Delta p/\Delta t$. In this way the surface force deflects the surface away from the denser medium, and thereby increases the optical path-length of the denser medium along the incident axis. By measuring the optical path-length shifts for different samples, their optical deformabilities may be compared.

The extent of the surface deflections (i.e., strain) of the objects are a function of the viscoelastic properties of the material. Comparing the response of two (2) objects with known optical characteristics under equivalent illumination conditions, allows a comparison of their viscoelastic response.

In the present invention, measurement is performed by quantifying the deflections of the object's surface due to the optically applied surface forces by imaging a sequence of phase-shifted replicas of the image of the object, and calculating the pixel by pixel optical path-length using an algorithm. The optical deformability observable contains a measure of the shape change (e.g., fractional change in optical path-length) at a given incident intensity (and beam profile). The optical path-length is defined as the true physical length of an object that the beam traverses, L, multiplied by its refractive index, n (i.e. optical path-length=nL). Thus, by measuring the optical path-length shifts for the object, such as a cancerous cell, and comparing it with that of other objects (i.e., non-cancerous cells), the optical deformabilities may be obtained, and carcinoma diagnosed.

In particular, detection of oral squamous cell carcinoma (OSCC) may be determined by the present technique. The resulting cancerous epithelial cells (which are adherent) are much more common than cancers derived from stromal cells like fibroblasts (i.e., sarcomas), and are prime candidates for the detection of carcinomas by this technique, which can interrogate such cells.

However, the present technique is also applicable to test any cell for any type of carcinoma (i.e., cancer derived from any type of epithelium of any organ such as breast, prostate, etc.).

Specifically, in the present invention, the objects (for example, cells—either provided from a patient or cultured cell lines) are formed on a monolayer on the surface of a substrate, and when light is applied to the objects, the photons will traverse the material of the indices $n_1$ (cell media), $n_2$ (cell) and $n_3$ (substrate). It should be appreciated that $n_2 > n_3$ otherwise the cells will come off the surface due to surface forces (i.e., otherwise the surface of the cell adjacent to the substrate will be pushed away from the substrate, causing detachment).

The objects or cells may also adhere to a layer of protein on the substrate so that strong cell-substrate interactions resist the detachment inducing force. For example, the cells may be adhered to a layer of laminin-5, collagen and/or fibronectin (e.g., extra-cellular matrix proteins). The resulting cell-substrate interactions may prevent the optical surface forces from causing the cell to detach from the protein covered substrate. The protein(s) may either be directly attached to the bare coverslip or a suitably treated surface on the coverslip.

Typical substrates such as glass or plastic do not have refractive indices ($n_3$) that are less than the cellular refractive indices ($n_2$). However, there exists a special class of amorphous fluoropolymers (i.e., Teflon® AF, Dupont) that have indices of refraction comparable to or less than water, and are transparent. Cells on a substrate of this type of amorphous fluoropolymer (which is chemically inert), will not come off the surface by the optical surface forces exerted on the cell at this boundary.

In the event that cells are not able to adhere onto a fluoropolymer substrate surface in a suitable manner, the surface may be coated with one of a variety of proteins, such as laminin-5, collagen I or fibronectin, to allow the cells to attach. The cells may be measured to be able to differentially detect normal and cancerous (i.e., OSCC, oral squamous cell carcinoma) epithelial cells via optical deformability.

In one embodiment, the optical deformability (a measure of cellular elasticity/viscoelasticity) of the cells is correlated with measurements of cytoskeletal protein expression (for example, fluorescence), and correlated with measurements of invasiveness, to determine if carcinomas are present.

Specifically, in one embodiment consistent with the present invention, FIG. 1 shows a schematic of an apparatus 100 for performing spatially modulated optical force microscopy (SMOFM) on adherent cells using holographic optical trapping technology.

However, one of ordinary skill in the art would know that the present invention may be performed on adherent cells using spatially modulated optical microscopy without the use of holographic optical trapping technology, or without the use of optically applied forces. Alternatively, if holographic optical trapping technology is used for applying optical forces, the present invention may be implemented without Fourier phase techniques as outlined in the present invention, and instead, utilize other quantitative phase microscopy techniques.

The laser-coupled spatially modulated optical force microscope (SMOFM) apparatus 100 of the present invention utilizes an inverted Nikon TE200 microscope 101, for example, with a temperature controlled sample stage 102 as the platform. The objects (i.e., adherent cells) 103, which are grown on an amorphous fluropolymer-coated cover glass or slide 104, or an amorphous fluoropolymer-coated cover glass or slide 104 coated with a protein as described above, for example, may be placed on the sample stage 102 (controlled to 37° C., for example).

In one embodiment, a lamp 105 of sufficient wattage is used to illuminate the objects 103 on the microscope slide 104, such that the objects 103 can be adequately viewed through an eyepiece 106 of the microscope 101, and through an imaging mechanism, such as a camera (CCD 107). This illumination by the lamp 105 may be eliminated, if so desired.

A low-coherence source, such as a superluminescent diode 108, is used for imaging (i.e., an OLSLD-820-HP1, Laser 2000, with a center wavelength of 820 nm, and 14 nm bandwidth). The superluminescent diode 108 provides wide-field illumination of the object 103 on the slide 104 with a narrow bandwidth and low coherence length in transmission, for the purpose of measuring the path length differences over the field of view—and is particularly suitable for spatial light modulated force microscopy techniques.

However, instead of a superluminescent diode 108, an alternative coherent light source, such as a suitable laser, may be used, for any of the quantitative phase microscopy techniques, including spatial light modulated force microscopy. The light from the superluminescent diode 108 is suitably collimated at the object plane, using a fiber-coupled collimator, for example, such that the diameter of the beam overfills the viewing area.

For a spatially modulated optical force microscope 101 with only one probe beam, the optical force laser (i.e., 1064 nm, V106C, Spectra-Physics) 109 is coupled into an objective 111 via the dichroic mirror 113 with a free-space beam or with a fiber optically-coupled beam. This beam is brought into focus at the back aperture plane of the objective 111 to generate a collimated beam from the objective lens 111. The laser beam may also be collimated or approximately collimated at the back-aperture plane so that the back-aperture is filled. This allows a converging beam to emerge from the objective 111. The laser 109 output power can be controlled by a calibrated, computer-controlled laser attenuator 119 (i.e., OZ Optics), placed at the output aperture of the laser 109, in order to control the magnitude of the optical force applied to the objects 103.

In order to provide a means to measure optical path lengths of a number of objects 103 on the slide 104 in parallel, a holographic optical trapping (HOT) apparatus 110 (see U.S. Pat. No. 6,055,106, to Grier et al., for example, which is herein incorporated by reference), is applied as a light source. The HOT light source which illuminates the objects 103 is a laser 109 (e.g., a 1064 nm, V106C, Spectra-Physics laser) which is used to apply an optically generated force.

For a spatially modulated optical force microscope 101 with a user-definable number of traps that can be dynamically changed, the HOT apparatus 110 may be utilized to modify the wavefront from the optical force laser 109 to apply points of light to locations of interest (e.g., where objects 103 or cells are present in the field of view).

Specifically, the HOT apparatus 110 (see FIG. 2) includes a collimated laser beam 201 which is shaped by a diffractive optical element 202 and transferred to a back aperture of an objective lens 203 via, for example, telescope lenses 204, 205 and dichroic mirror 206, and focused into a plurality of optical traps 207, which are illuminated by beam 208. The point B' is conjugate to B. Note, however, that telescope lenses 204, 205 may be eliminated from the apparatus, if desired.

Figure 2:
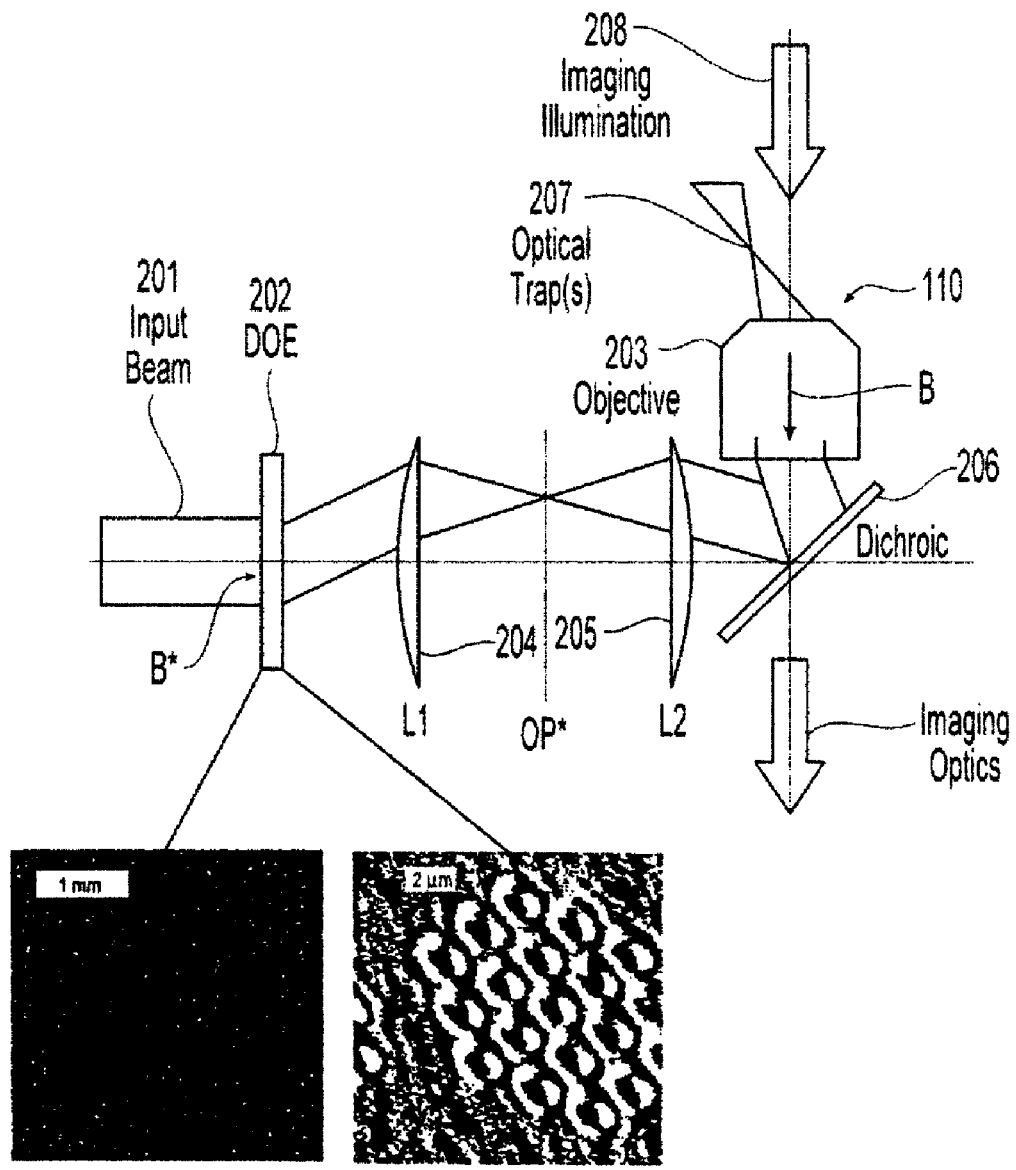
FIG. 2 shows an exemplary holographic optical trapping system which is a part of the apparatus of FIG. 1, according to one embodiment consistent with the present invention.

In FIG. 1, some elements of the HOT apparatus 110 of FIG. 2 are shown. For example, the objective lens 203 is a microscope objective lens 111, which focuses the light beam 208 to form optical traps 207 which affect the objects 103 on the slide 104.

Thus, objects 103 (e.g., cells) on the slide 104 may have pressure applied to them by using the HOT apparatus 110 as a high intensity source (i.e., laser 109, for optical probing). This pressure is directed to each of the objects 103 on the slide 104.

Further, to perform the measurement of the optical path lengths of the objects 103 or cells more efficiently, holographic optical techniques are used to parallelize the optical force probes. By using the computer-controlled SLM 115 to control the phase profile of a single laser's 109 wave-front, it is possible to position and apply multiple optical force probes in a field of view simultaneously.

Further, since the detection method employing the spatially modulated optical force microscopy technique measures the optical path-lengths for the whole field of view at once, pixel by pixel, the present invention will be easily scalable to measure many objects 103 or cells in parallel (also, with automation, if desired). Thus, many objects 103 or points within the object sample 104 (e.g., cells) may be probed simultaneously by creating many probe beams (beamlets) with a single source (using HOT 110, for example).

In the present invention, illumination of the objects 103 is achieved by a lamp 105 which has a bandpass filter 114 that is placed after it, and which allows a visible band of light to emerge from the lamp 105 through to the viewing camera (CCD) 107. A similar bandpass filter is placed before the viewing camera to exclude the other two light sources (i.e., the laser 109 and the superluminescent diode 108). As stated above, this visible band of light is for viewing by the user and may be omitted from the apparatus, if desired.

Figure 3:
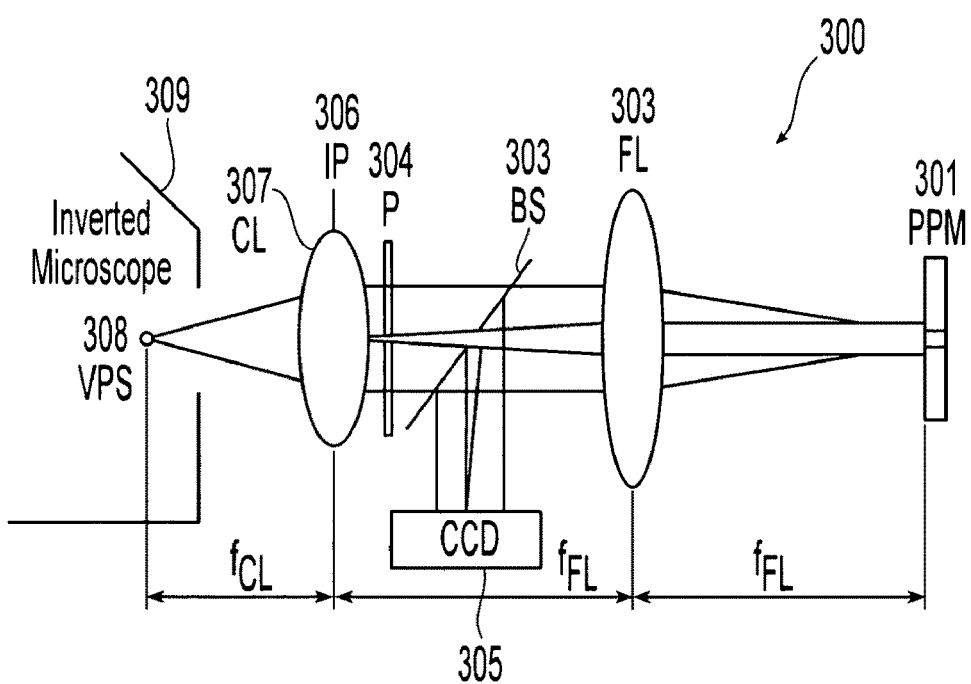
FIG. 3 shows a diagram of optical components necessary to perform spatial light modulated optical force microscopy, including Fourier transformation of an image, the components which are partially included in the apparatus of FIG. 1, according to one embodiment consistent with the present invention.

The transmitted light from the superluminescent diode 108 is imaged as a superposition of the unmodified image plus a phase shifted version of the image, and is accomplished by a spatial light modulator (SLM) 115, also known as a programmable phase modulator (PPM) (i.e., a X8267 Hamamatsu Photonics, K.K.), which is part of the SMOFM 300 shown in FIG. 3. The transmitted light passes through bandpass filter 118 which allows only light from the superluminescent diode 108 to be imaged on imaging mechanism or CCD 116, and blocks laser 109 light, and lamp 105 light from reaching the CCD 116.

A computer with computer-controlled interface 117 integrates the SLM 115, CCD 116 image acquisition, HOT 110 and laser attenuator 109 control (e.g., from OZ Optics), and image processing necessary for position dependent optical path length calculations, and may have software written in a graphical programming language.

In the present invention, measurements of the optical deformations of the object 103 are performed using spatially modulated optical force microscopy (SMOFM). As stated above, SMOFM quantitatively measures the optical path length changes as a result of the optical forces applied by the HOT 110.

The present technique involves the introduction of a second light source (i.e., the low coherence superluminescent diode 108), which is fiber collimated after emerging from a single mode fiber (ensuring spatial coherence). The superluminescent diode 108 provides plane wave illumination of the objects 103 with spatially coherent light, and the low temporal coherence of the light from diode 108 prevents problematic reflection artifacts during detection. A Fourier transform of the image field is projected onto the surface of the SLM 115. This image is then back transformed to form a real image of the objects 103 on CCD 116. Without any modulation on the SLM 115, the original image is reconstructed on the CCD 116. By modulating only the k=0 component of the SLM 115 (given by pixels in the central spot), the phase of the DC level of the image may be modulated independently of the spatially varying component 115.

The present technique includes stepping the phase of the DC component of the image through four (4) phase shifts (of $\pi/2$ each) and capturing the resultant four (4) CCD images which store the interference of the DC and spatially varying fields of the image, pixel by pixel.

Existing algorithms (see equations [1] to [4] below) are used to obtain the phase difference between the DC field and spatially varying field, pixel by pixel, using the four (4) images obtained. This phase-shift is equivalent to the optical path-length shift undergone by the light at that pixel location.

By the mathematical relationships below (equation [3]), the information from four (4) phase shifted images can be expressed as a phase distribution of the E field. And by comparing the phase distribution before and after optical forcing, the desired pixel by pixel optical path-length shift information is acquired.

For example, the electric field in the image plane is $E=E_0+E_1$, where the total field E is split into a spatially non-varying field (DC component) $E_0$ and a spatially varying component $E_1$. The intensity measured on the CCD 116 for each of the four (4) phase shifts (n=0, 1, 2, 3) is given by:

$$I(x,y;n)=|E_0|^2+|E_1(x,y)|^2+2|E_0||E_1(x,y)|\cos[\Delta\phi(x,y)+n\pi/2],\text{ where } n=0,1,2,3. \quad [1]$$

$\Delta\phi(x,y)$ is the phase difference between $E_0$ and $E_1(x,y)$ at pixel position (x,y), and is given by:

$$\tan(\Delta\phi(x,y))=[I(3)-I(1)]/[I(0)-I(2)]. \quad [2]$$

The phase distribution of the E field, $\phi(x,y)$ is given by, $$\phi(x,y)=\tan^{-1}\{\beta(x,y)\sin[\Delta\phi(x,y)]/(1+\beta(x,y)\cos[\Delta\phi(x,y)])\}, \quad [3]$$

and $$\beta(x,y)=|E_1(x,y)|/|E_0|=\gamma[I(x,y;0)-I(x,y;2)+I(x,y;3)-I(x,y;1)]/[\sin[\Delta\phi(x,y)]+\cos[\Delta\phi(x,y)]], \quad [4]$$

where $\gamma=\frac{1}{4}|E_0|^2$.

By these existing mathematical relationships (see Popescu, G., et al., "Fourier phase microscopy for investigation of biological structures and dynamics", Optics Letters 29 (21): 2503-5 (2004)), the information from the four (4) phase shifted images can be expressed as a phase distribution of the E field. By comparing the phase distribution before and after optical forcing, the desired pixel by pixel optical path-length shift information is acquired.

Accordingly, in the present invention, the image signal from the superluminescent diode 108 is modified by first placing a correcting lens (CL) 307 (see FIG. 3) at the focal plane of the image (CL 307 may be selected to have a focal length equal to the image plane (IP) 306-virtual point source (VPS) 308 distance). Then the image is Fourier transformed using a Fourier lens 302 (e.g., focal length of 50 cm), using standard 4-f geometry, onto the surface of the SLM or PPM 301 (SLM 115 in FIG. 1).

The spatial light modulator SLM 115 (i.e., programmable phase modulator (PPM) (i.e., a X8267 Hamamatsu Photonics, K.K.)) may be an individually addressable 2-dimensional liquid crystal array, which is designed to have independent phase control between 0 to $2\pi$ with at least 8 bit resolution for each pixel. This phase control is possible by selecting the polarization of the incident light to match the direction of the molecular axis of the liquid crystal by inserting a polarizer P 304. The phase modulated image that is reflected off the SLM 301 is imaged onto a CCD camera 305 (CCD 116 in FIG. 1) by reflection off a beam splitter (BS) 303 onto the CCD 116.

Thus, the measurement of each object 103 may include 1) measurement of the optical path-length of the object 103 when no optical force is present (yielding optical path-length L), and 2) measurement of the optical path-length of the object 103 after an optical force is applied (yielding optical path-length L'). The technique of the present invention will yield a measurement of the optical deformability (i.e., strain, (L'-L)/L). The strain measurement of sample cells may be compared to strain measurements of carcinoma cells to determine if they are cancerous. The duration and magnitude of the applied optical force will determine the magnitude of the elastic and/or viscoelastic response from the object 103 is elicited, and whether the magnitude of the elastic and/or viscoelastic response is indicative of carcinoma.

In another embodiment, the optical deformability of the objects or cells may be measured and correlated with measurements of cytoskeletal/structural protein expression (via fluorescent microscopy of cells). For example, there are many methods known in the art for using fluorescence to image and quantify protein expression using immunolocalization (see Imai, K., et al., "Immunolocalization of desmoglein and intermediate filaments in human oral squamous cell carcinomas", Head Neck 17:204-12 (1995)).

Further, it has been shown that cancerous oral epithelial cells express vimentin. There have also been reports suggesting that vimentin expression is detectable even before the tumor cells exhibit a mesenchymal morphology, which makes the hypothesized vimentin mediated change in cellular deformability a potentially desirable diagnostic marker.

To correlate protein expression through immunolocalization, one could incubate cells with specific antibodies (i.e., anti-vimentin), wash the cells, then incubate the cells with fluorescently labeled secondary antibodies, such as Alexa Fluor 594 secondary antibody, wash and finally prepare the cells for fluorescent image analysis in combination with SMOFM.

In a similar way, the technique of the present invention may be used to correlate any desirable protein expression marker with the optical deformability of cells.

In other embodiments consistent with the present invention, different techniques may be used for quantitatively measuring the optical path length, as opposed to using the above-described Fourier Phase technique which requires the numerical processing of four (4) images which are acquired in synchrony with four (4) holograms presented to the Spatial Light Modulator (SLM) 301.

Since speed in quantitative imaging is important, and since four (4) images are required to generate one (1) phase profile of the object(s) in the field of view in the Fourier Phase technique, alternative methods which address providing increased speed, are desired. Further, when seeking to measure dynamic events or measure phase profiles with higher time resolution, other techniques which can extract the phase profile from one image only, are also highly desired.

Figure 4:
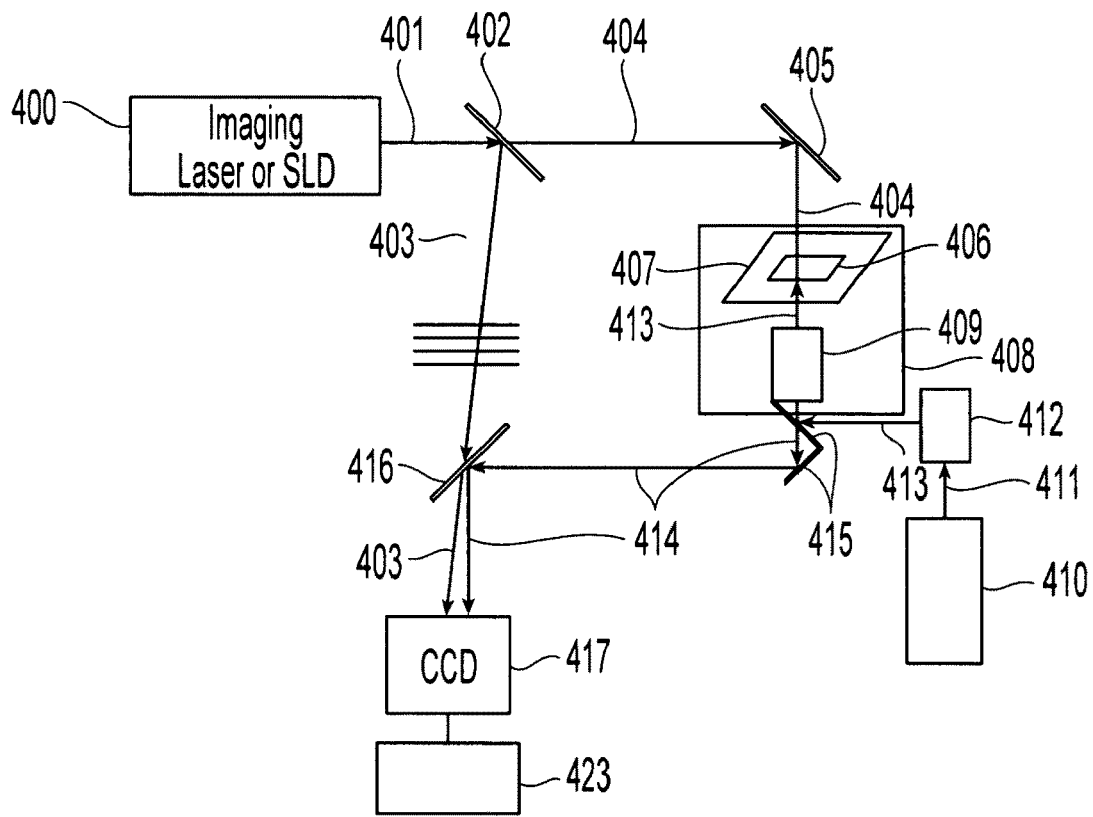
FIG. 4 shows a diagram of a holographic optical forcing array and an adaptation of a digital holography apparatus for dynamic cellular probing and diagnostics, according to another embodiment consistent with the present invention.

In another embodiment consistent with the present invention, a novel adaptation of digital holography is used to detect the optical deformability of objects or cells. Specifically, in the present invention, as shown in FIG. 4, an imaging laser or superluminescent diode (SLD) 400, such as the OLSLD-820-HP1, Laser 2000, discussed above, is used to provide illumination of the objects or cells 406 on the microscopic slide 407 of a microscopy apparatus 408, such as the Nikon TE200 microscope discussed above. As stated above, the SLD 400 has a narrow bandwidth and low coherence length, and emits a laser beam 401 which can be split and then recombined to form an interference pattern, which can be quantitatively analyzed to determine whether there is deformation of the objects or cells 406. As with the previous embodiments, instead of a superluminescent diode 400, an alternative coherent light source, such as a suitable laser, may be used.

Specifically, the SLD 400 emits a laser beam 401 which is split by a beam splitter 402 into a reference beam 403 and an object beam 404. The object beam 404 is redirected by mirror 405, and has its wave-front distorted after being transmitted through the sample 406 of object(s) or cell(s) disposed on the microscopic slide 407 of an optical microscopy apparatus 408, such as the Nikon TE200 microscope discussed above. Further, as stated above, the microscopy apparatus 408 may include a temperature and atmosphere controlled sample stage as the platform. Also as stated above, the objects (i.e., adherent cells) 406, may be grown on, for examples: an amorphous fluoropolymer-coated cover glass or slide 407, or an amorphous fluoropolymer-coated cover glass or slide 407 coated with a protein as described above, or on an alternatively coated/treated cover glass or slide 407 coated with protein, either of which may be placed on the sample stage (controlled to 37° C., for example).

The object beam 404 then passes through the sample 406 on the slide 407 into the objective lens 409 of the microscopy apparatus 408. The objects 406 can be adequately viewed through an eyepiece of the microscope (see FIG. 1). The resulting beam 414 is redirected by another dichroic mirror 415 to beam splitter 416, which directs it to detector 417 (e.g., CCD camera) to be imaged.

Simultaneously, a continuous wave (CW) forcing laser such as the 1064 nm, V106C, Spectra-Physics laser or pulsed laser 410, emits a laser beam 411 which reflects off of a spatial light modulator (SLM) 412, is diffracted, and the diffracted beamlets 413 are coupled into the objective lens 409 via dichroic mirror 415. The beamlets provide optical force points on the sample objects or cells 406. Thus, the object beam 404 illuminates a sample 406 whose objects or cells are under optical forcing.

Simultaneously, the reference beam 403 from beam splitter 402, whose wavefront is undistorted, passes through beam splitter 416 into detector 417.

Accordingly, the reference beam 403 is temporally coherent with the object beam 414, so that an interference pattern is generated at the detector 417 (e.g., CCD, CMOS video camera), and the object beam 414 and reference beam 403 are combined in an off-axis geometry at the detector 417 (i.e., the beams are not exactly parallel when they interfere at the detector 417). The interference pattern at the detector 417 is given by the superposition:

$$H=|E_O+E_R|^2,$$

where H is the hologram, $E_O$ is the E field of the beam 404 transmitted through the sample 406 and $E_R$ is the E field of the reference beam 403.

The hologram H stored in the detector image may be numerically reconstructed by several methods, including the following.

In one step, the product of the hologram H with a reference wave R, is Fourier transformed: $\mathcal{F}(H \cdot R)$.

In another step, the impulse response function for free-space propagation evaluated at the desired reconstruction distance d is Fourier transformed: $\mathcal{F}(P;d)$.

In yet another step, the product of the above two Fourier transforms is inverse Fourier transformed as follows:

$$B=\mathcal{F}^{-1}(\mathcal{F}(H \cdot R) \cdot \mathcal{F}(P;d))$$

which yields the complex field amplitude of the numerically reconstructed object field at a distance determined by the reconstruction distance variable d set in the impulse response function.

The intensity and phase profile of the numerically reconstructed object field is then simply:

$$I(x,y)=|B(x,y)|^2,$$

$$\phi(x,y)=\arctan(Im(B(x,y))/Re(B(x,y)));$$

where x and y are the image coordinates at the reconstructed distance d.

The optical reference beam $E_R$ and the numerical reference beam R should be chosen so that the reconstructed real image does not interfere with the reconstructed imaginary image nor the DC term. The DC term may also be numerically removed by subtracting the average value of the product H·R from each pixel value, i.e., $$H \cdot R_{DC\ suppressed}=H \cdot R-\mathrm{avg}(H \cdot R).$$

With the review of the interference pattern at the detector 417, the deformation in shape of the objects or cells 406 can be calculated and quantitatively determined using computer 423. Since the interference pattern must be analyzed and quantitatively determined, the calibration of the equipment, must be accurate.

Accordingly, the quantitative phase profile of the objects or cells 406 may be obtained from the interference pattern of the images of the objects or cells 406 at the detector 417 using standard techniques. Thus, in the present embodiment, the phase is not controlled as in the previous Fourier phase method, but rather, visual changes are noted with respect to the deformation of the objects or cells 406 in the sample.

As stated above, in an alternative embodiment, a single beam optical force probe may be applied without a spatial modulating component (i.e., without SLM 412), and in another embodiment, with a moving sample holder or stage 102 (as part of apparatus 408), to move the object(s) 406 to the location of the forcing beam (i.e., beam 413 is stationary, the sample (on slide 104) is moved).

In yet another embodiment, the single beam optical force probe may be directed to cell(s)/object(s) 406 of interest via movable mirrors, acousto-optic modulators (AOMs) or other suitable devices 410, allowing the optical forcing laser 410 to direct its single beam to the object(s) of choice. This would allow a sequential application and measurement of optical forces of the object(s) 406 in the field of view.

In yet another alternative embodiment of FIG. 4, the invention is implemented in an endoscope for endoscopic measurements (i.e., measurements inside the human body).

In an alternative embodiment, dynamic deformation information (e.g., allowing viscoelastic parameters to be measured) may be obtained by acquiring images that freeze the deformation of the objects 406 (i.e., cells) using either a fast detector camera 417 (i.e., high frame-rate, fast shutter) and/or pulsed laser as an illumination source (i.e. strobe effect) instead of laser 400. A pulsed optical forcing laser 410 may also be used instead of a CW laser for applying impulses of force whose response may be measured with a pulsed imaging laser and/or fast detector camera.

In the present embodiment, there is an identical capability for optical forcing and application of optical pressure on the cell(s)/object(s) 406. However, instead of using the Fourier phase microscopy technique for quantitative measurement of the phase profile of the cells'/objects' 406, this embodiment utilizes digital holography as the method for quantitative phase measurement. In conventional digital holography, the cells 406 are visualized only, with the optical phase profile of the image quantitatively measured, without the application of optical forces via HOT or otherwise. The advantage of the present invention is that only one image is needed to generate the phase profile, instead of four images as in the Fourier phase microscopy technique of the previous embodiment when determining the optical phase profile with and without the application of optical forces. This makes the data acquisition faster and more efficient.

In yet another embodiment consistent with the present invention, and based on the same principles as in the previous Fourier Phase embodiment, a modified technique for quantitatively measuring the optical path length as opposed to using the above-identified Fourier Phase technique, is a method called phase-stepped holography, which allows the phase profile of an object or cell 406 (e.g., observed under a microscope 408) to be measured using only one (1) image.

As stated above, a limitation of the Fourier Phase technique is the speed of quantitative imaging, since 4 images are required to generate 1 phase profile of the object(s) in the field of view. When seeking to measure dynamic events or measure phase profiles with higher time resolution, other techniques which can extract the phase profile from one image only, are superior.

Figure 5:
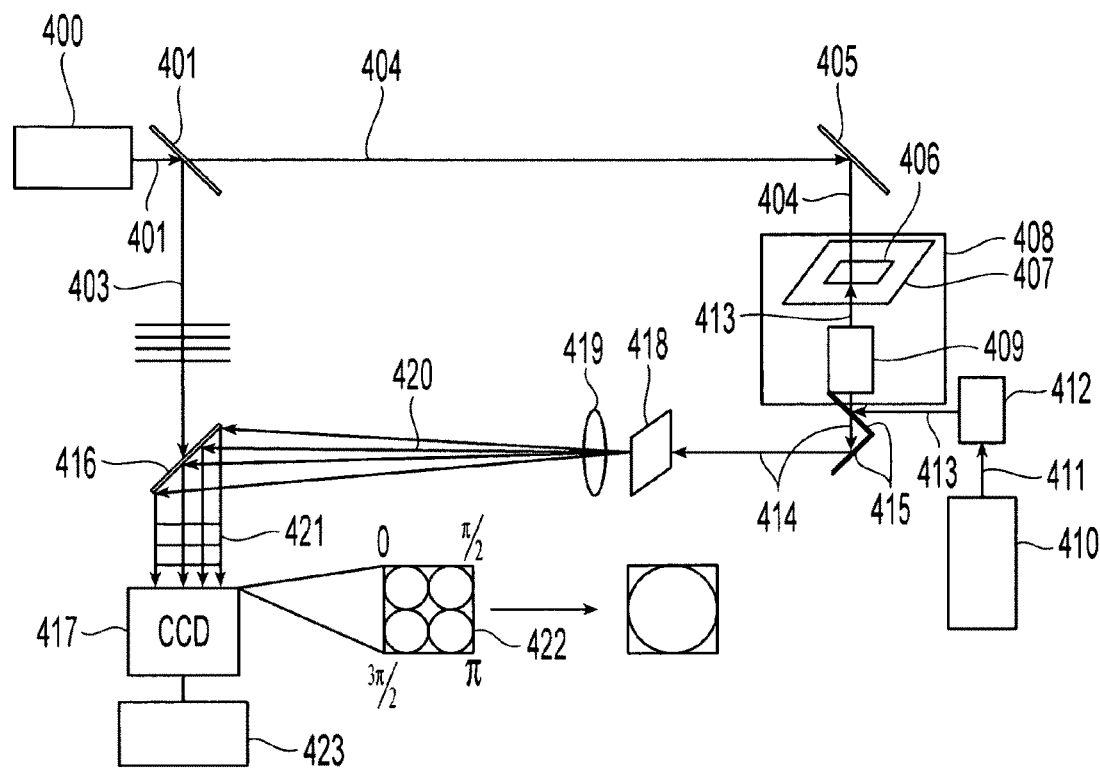
FIG. 5 shows a diagram of a holographic optical forcing array and a holographic phase-stepped apparatus for dynamic cellular probing and diagnostics, according to yet another embodiment consistent with the present invention.

The present invention uses holographic phase-stepped interferometry to achieve dynamic cellular probing and diagnostics. As shown in FIG. 5, this technique is similar to the adaptation of digital holography of FIG. 4, in that a reference beam 403 and an object beam 404 are generated and interfered by a SLD 400—namely, an object beam 414, which is transmitted through the sample 406 (e.g. cells 406), and a reference beam 403, which is split off from the main beam 401, and is temporally coherent with the object beam 414, so that an interference pattern is generated at the detector (CCD) 417.

However, an important feature of the apparatus of this embodiment is a holographic optical element 418 (i.e., SLM) and transfer lens 419, which are inserted between the object beam 414 and beam splitter 416, and which diffracts the beam into several beamlets 420 before being directed by the beam splitter 416 into the detector 417.

Thus, the holographic optical element 418 splits the beam 414 and makes replicas 420 of the beam in space (i.e., phase-stepping the image in space), instead of resulting in phase shifts in time, as in the Fourier phase microscopy technique disclosed above. Thus, the phase-delayed or phase-stepped replicas 420 of the image of the objects 406 are diffracted into four quadrants of the detector 417, and simultaneously interfered with the reference beam 403. Each replica 421 is phase shifted by π/2, and a computer 423 computes the phase profile of the objects 406 from the four holographically phase-stepped replica images 422 interfered with the reference beam 403 (taken from each quadrant of the detector 417).

Thus, this embodiment provides the advantage that only one image is used to capture all four phase shifted images, and thus allowing the phase profile of an object to be measured using only one image—which provides greater speed and efficiency. The measurement of the phase profile and the optical path lengths is the same as discussed above in the Fourier phase microscopy method.

As stated above with respect to the embodiments of FIGS. 4 and 5, a pulsed laser 410 may be used as a source for the optical forces that impart deflections on the sample 406 (e.g., cells). The amount of the deflection is quantitatively measured by the probe laser configuration 410 shown in FIGS. 4-5. The deflection can be generated by a high peak-power pulsed laser 410 which emits pulses of short duration (e.g., nanosecond). The impulse from one of these pulses is significant enough to cause a deflection in the soft sample 406 (e.g., cell).

After the pulse, the deformation response of the sample 406 (e.g., cell) is captured by a regular or high-speed detector 417 (i.e., CCD—image acquisition started by output synchronization pulse from the pulsed laser 410) using a pulsed or CW low-coherence illumination source (e.g., SLD 400). With respect to the embodiment shown in FIG. 5, using the holographic phase-stepping technique, the optical phase delay for each pixel for each CCD frame of the detector 417 can be measured and calculated, giving a pixel-wise viscoelastic measurement.

A sequence of CCD frames taken after the pulsed laser force impulse may be taken, generating a time-course for the deflection relaxation (as measured by the phase delay) for each pixel of the image, allowing the viscoelastic response of the objects 406 or regions in the image to be measured. The viscoelastic relaxation data may give a more distinct signature to disease state and/or disease progression than the static deflection measurements of conventional methods.

Figure 6:
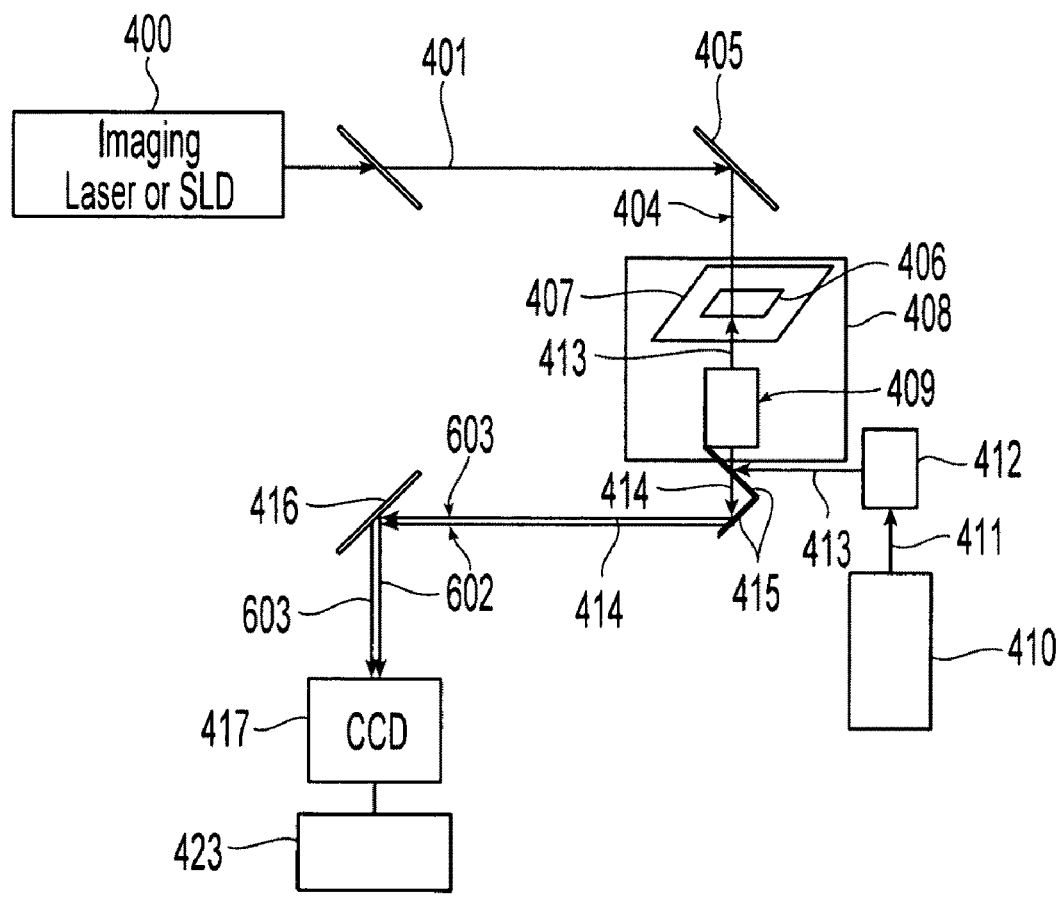
FIG. 6 shows a diagram of a holographic optical forcing array and an in-line holography apparatus for dynamic cellular probing and diagnostics), according to yet another embodiment consistent with the present invention (via bead displacement measurements from the bead scattering holograms generated by the interference between the bead-scattered and unscattered reference beams).
Figure 7:
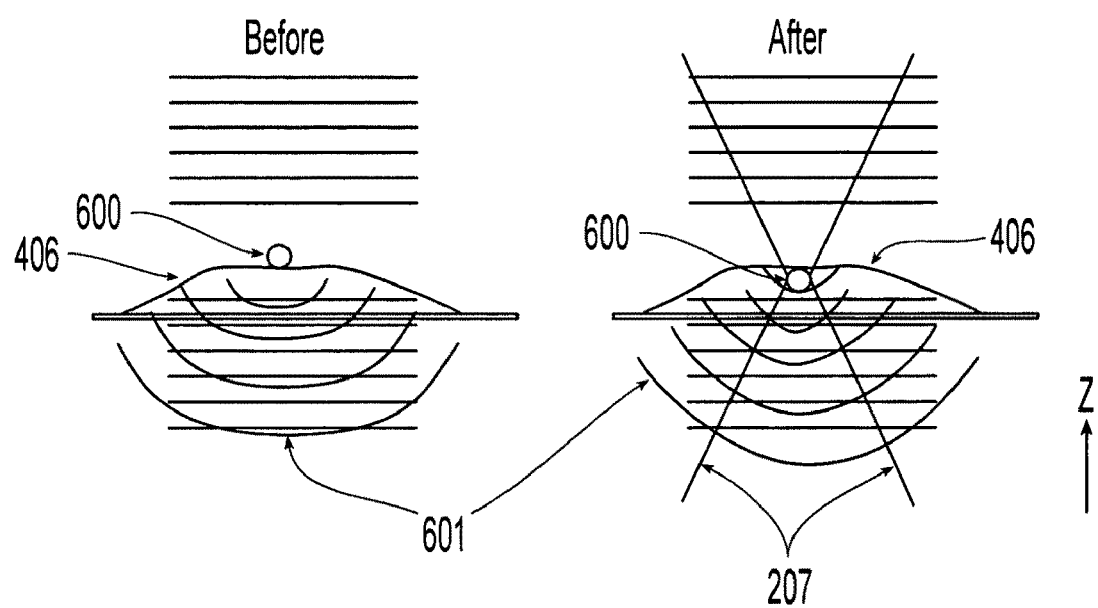
FIG. 7 shows a diagram of a holographic optically trapped bead before and after cell deformation, depicting holographic interference patterns of bead scattering (i.e., Mie scattering), in accordance with the methods and apparatus of FIG. 6.

Based on the same principles as described above, in yet another embodiment consistent with the present invention, a modified technique for quantitatively measuring the optical path length changes upon application of the optical forces is presented. This embodiment utilizes beads 600 (e.g., micron diameter silica beads) placed on the surface of the cell(s)/object(s) 406 to be probed (see FIGS. 6 and 7). The optical forcing array applies optical forces to these beads 600 thereby deforming the underlying cell(s)/object(s) 406 (see FIG. 7). The optical forcing array may also pre-position the beads 600 on the cells 406 before the beads 600 are pressed into the cells 406. The bead's 600 position may be determined by applying Mie theory to the in-line holographic images of the beads 600 (for example, see "Characterizing and tracking single colloidal particles with digital holographic microscopy", Lee, Sang-Hyuk; Roichman, Yohai; Yi, Gi-Ra; Kim, Shin-Hyun;

Yang, Seung-Man; van Blaaderen, Alfons; van Oostrum, Peter; Grier, David G, Optics Express, Vol. 15 Issue 26, pp. 18275-18282 (2007)), which are interference patterns 601 between the wave 602 diffracted by the bead and the undiffracted wave 603. The imaging laser (see FIG. 6) (e.g., superluminescent diode 400, or low-coherence length laser) is used in transmission-mode and is the source that generates the holographic images on the detector (CCD) 417.

Analysis of the interference fringes by Mie theory yields the three dimensional position of the bead 600 (among other variables). By comparing the z position (z direction parallel to optic axis) of the beads 600 before and after the optical trap 207 is applied to the bead 600, a measurement of the deformation displacement on the surface of the cell/object 406. This displacement, in addition to the knowledge of the trap power/optical trapping force and an estimate of the contact area between the bead 600 and cell/object 406 allows a measurement of the elastic modulus (e.g., Young's modulus). A background image may also be taken, for correction purposes without the bead 600, which takes into account the scattering due to the cell(s)/object(s) 406 alone.

Dynamic deformation information (e.g., allowing viscoelastic parameters to be measured) may be obtained by acquiring images that freeze the object's 406 deformation using either a fast detector camera (i.e., high frame-rate, fast shutter) and or pulsed laser as an illumination source 400.

Thus, the various embodiments of the present invention allows optical forces to be applied to objects, for example, and their resultant surface deflections may be sensitively and quantifiably measured. The present invention allows quantification of the deflections of the cell surface due to optically applied surface forces, to be detected with interferometric sensitivity (sub-nanometer sensitivity). The change in optical path lengths or quantitative changes in the shape of the cells, may be determined, so that diseased cells, including cancer cells, that have a unique optical deformability signature may be identified.

Thus, the present invention is a valuable tool for correlating molecular and genetic patterns in cells with optically generated mechanical deformability measurements, adding a new dimension to the characterization of cancerous phenotypes. The present invention also provides a basis for a cancer screening assay based on a deformability measurement parameter.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. An apparatus for detecting optical deformation in a sample contained on a sample holder, said sample containing at least one object, comprising:
    a light source which emits a first light beam which illuminates at least one stationary object on the sample holder;
    an optical forcing mechanism which provides an optically generated force on the at least one object to perturb the at least one object, said optical forcing mechanism including:
        a laser which emits a second light beam onto the at least one object; and
        a spatial light modulator which diffracts said second light beam and which applies the optically generated force to the object and generates a superposition of an unmodified image of the object and a phase-shifted or diffracted version of said image of the at least one object; and
    a detector which detects an interference pattern between a first portion of said first light beam which is undiffracted, and a second portion of said first light beam which is diffracted by the at least one object in the sample,
    wherein in said superposition of said unmodified image and said phase-shifted or diffracted image, said detector determines an optical path length change as a result of said optically generated force on the at least one object, said optical path length change yielding an optical deformation of the at least one object.

2. The apparatus according to claim 1, wherein said optical forcing mechanism further comprises:
    a microscope, including an objective lens;
    wherein said second light beam is a collimated light beam; and
    a diffractive optical element which shapes said second light beam and transfers said second light beam to a back aperture of said objective lens;
    wherein said objective lens focuses said collimated light beam to form an optical force array which perturbs the at least one object on the sample holder.

3. The apparatus according to claim 2, wherein said optical forcing mechanism is a holographic optical trapping apparatus which uses said diffractive optical element to diffract said second light beam into multiple diffracted beamlets, and where said diffracted beamlets are applied to said at least one object to impart forces onto the at least one object.

4. The apparatus according to claim 3, wherein said diffracted beamlets apply forces normal to an object plane and act as optical force probes which apply pressure to the at least one object in the sample simultaneously.

5. The apparatus according to claim 4, further comprising:
    a first dichroic mirror, which directs the diffracted second light beam into said objective lens; and
    a second dichroic mirror, which directs said first light beam from said first light source to said detector after having passed through the sample holder.

6. The apparatus according to claim 5, wherein a first portion of said first light beam which is undiffracted, is transmitted through the sample containing the at least one object without being diffracted by said at least one object, to yield an undiffracted reference beam which later recombines and interferes with a second portion of said first light beam that is diffracted by the at least one object, yielding said interference pattern.

7. The apparatus according to claim 6, further comprising:
    at least one bead, said bead which is placed on a surface of the at least one object, and to which said optical forcing mechanism applies said optically generated force;
    wherein said optically generated force on said at least one bead exerts pressure on the at least one object underlying said at least one bead to deform the at least one object.

8. The apparatus according to claim 7, wherein a three-dimensional position of each said at least one bead is determined by applying Mie theory to an in-line holographic image of said bead, which is an interference pattern between a diffracted beam and an undiffracted beam.

9. The apparatus according to claim 8, wherein a measurement of deformation displacement on said surface of said at least one object is performed by determining said position of said bead before and after an application of said optically generated force.

10. The apparatus according to claim 6, further comprising:
a mirror which directs said undiffracted and diffracted light beams from said first light source, via said second dichroic mirror, to said detector.

11. The apparatus according to claim 5, further comprising:
a first beam splitter which splits said first light beam into a reference beam and an object beam, said object beam which illuminates said at least one object, and said reference beam which is undiffracted and directed to said detector;
wherein said object beam and said reference beam are combined in an off-axis geometry at said detector; and
wherein said detector detects said interference pattern between said reference beam and said object beam.

12. The apparatus according to claim 11, wherein said second dichroic mirror directs said object beam to said detector.

13. The apparatus according to claim 12, further comprising:
a second beam splitter which directs said reference beam from said first beam splitter, and said object beam from said second dichroic mirror, to said detector.

14. The apparatus according to claim 13, wherein at said detector, said reference beam is temporally coherent with said object beam, such that said interference pattern is generated at said detector; and
wherein a quantitative phase profile of said at least one object is obtained from said interference pattern.

15. The apparatus according to claim 13, further comprising:
a holographic optical element disposed between said second dichroic mirror and said second beam splitter, which diffracts said object beam into four beamlets and directs said beamlets to said second beam splitter and to said detector, generating four spatially phase-stepped replicas of said object beam.

16. The apparatus according to claim 15, wherein said holographic optical element makes phase-stepped replicas of images of said at least one object which are diffracted into four quadrants of said detector and simultaneously interfered with said reference beam.

17. The apparatus according to claim 16, further comprising:
a computer having a program which computes a phase profile of said at least one object from said four holographically phase-stepped replica images interfered with said reference beam.

18. The apparatus according to claim 15, further comprising:
a transfer lens disposed between said holographic optical element and said second beam splitter.

19. The apparatus according to claim 15, wherein a measurement of a phase distribution before and after optical forcing of said at least one object, provides an optical path-length shift determination which denotes an optical deformability of said at least one object.

20. The apparatus according to claim 4, further comprising:
a laser attenuator disposed at an output aperture of said laser, to control a magnitude of the optically generated forces applied to the at least one object.

21. The apparatus according to claim 3, wherein said optical deformability is based on a surface deflection of the object in response to said optical force probes, said surface deflection which is a function of the viscoelastic response of the at least one object.

22. The apparatus according to claim 21, wherein a comparison of two objects with known optical deformation characteristics under equivalent illumination and optical forcing conditions, compares their viscoelastic responses.

23. The apparatus according to claim 3, wherein said light source measures optical path lengths of the at least one object over a field of view, pixel by pixel, according to spatial light modulated force microscopy techniques.

24. The apparatus according to claim 23, wherein said holographic optical trapping apparatus illuminates the at least one object and modifies a wavefront from said laser to apply points of light to locations of interest where the at least one object is present in said field of view.

25. The apparatus according to claim 2, wherein said at least one object is an adherent cell disposed on the sample holder.

26. The apparatus according to claim 25, wherein said at least one cell is grown on an amorphous fluoropolymer-coated cover glass.

27. The apparatus according to claim 25, wherein said at least one cell is grown on a cover glass coated with protein.

28. The apparatus according to claim 25, further comprising:
a movable sample stage which moves said sample to a location of said second light beam of said optical forcing mechanism.

29. The apparatus according to claim 28, wherein said sample stage is temperature-controlled.

30. The apparatus according to claim 25, wherein optical path length of the adherent cell is measured when no optically generated force is present, and measured after an optically generated force is applied, to yield an optical deformability of the adherent cell, which is compared with measurements of carcinoma cells to determine whether the adherent cell is cancerous.

31. The apparatus according to claim 30, wherein carcinoma cells express a cytoskeletal protein including vimentin, and wherein said cytoskeletal protein mediated change in cellular deformability is used as a diagnostic marker.

32. The apparatus according to claim 2, further comprising:
a mechanism which moves said second light beam of said optical forcing mechanism, said mechanism including movable mirrors and acousto-optic modulators.

33. The apparatus according to claim 1, wherein said light source is an imaging laser or a superluminescent diode which illuminates the at least one object with spatially coherent light.

34. The apparatus according to claim 33, further comprising:
a correcting lens which modifies an image signal from said superluminescent diode, said lens which is placed at a focal plane of an image generated therefrom.

35. The apparatus according to claim 1, further comprising:
a computer having a program which analyzes said interference pattern.

36. The apparatus according to claim 1, wherein said detector is one of a high-speed or fast-detector camera.

37. The apparatus according to claim 1, wherein said laser is a forcing laser, and said forcing laser is a continuous wave or pulsed forcing laser.

38. The apparatus of claim 1, wherein said apparatus is an endoscope.

39. The apparatus according to claim 1, wherein optical deformability is correlated with measurements of cytoskeletal protein expression and correlated with measurements of invasiveness, to determine whether carcinomas are present.

40. The apparatus according to claim 1, further comprising:
a lamp which illuminates the at least one object on the sample holder.

41. The apparatus according to claim 40, further comprising:
a first bandpass filter disposed in front of said lamp, which allows a band of light to be transmitted to said detector.

42. The apparatus according to claim 41, further comprising:
a second bandpass filter disposed before said detector to exclude said second light beam from laser and said first light beam from said light source.

43. The apparatus according to claim 1, wherein said phase-shifted or diffracted image is generated by stepping a phase of the DC component of the unmodified image through four phase shifts, and capturing the resultant four images, which store an interference of same, pixel by pixel, and obtaining a phase difference between them.

44. An apparatus for detecting optical deformation in a sample contained on a sample holder, said sample containing at least one object, comprising:
a light source which emits a first light beam which illuminates at least one stationary object on the sample holder;
an optical forcing mechanism which provides an optically generated force on the at least one object to perturb the at least one object
means for measuring an optical deformability of the at least one object, said measuring means including a measurement mechanism which measures a phase profile of the object to determine an optical path length change of the object after application of said optical forcing mechanism.

45. A method of detecting deformation in at least one object of a sample, comprising:
illuminating at least one stationary object on a substrate using a first light beam generated by a light source;
applying an optically generated force on said at least one object, to perturb the object, using a second light beam generated by a laser of a holographic optical trapping apparatus; and
measuring an interference pattern in a superposition of an unmodified image and a phase shifted or diffracted image at a spatial light modulator, using a detector, to determine an optical path length change as a result of said optically generated force on the object, said optical path length change yielding an optically measured deformation of the at least one object.

46. The method according to claim 45, wherein said applying step comprises:
diffracting said second light beam into multiple diffracted beamlets using a diffractive optical element of said holographic optical trapping apparatus; and
applying said diffracted beamlets to said at least one object to impart forces onto said at least one object.

47. The method according to claim 46, further comprising:
parallelizing said optical forces on the at least one object using said diffracted beamlets, said diffracted beamlets acting as optical force probes which apply pressure to the at least one object in the sample simultaneously.

48. The method according to claim 47, wherein said optical deformability is based on a surface deflection of the at least one object in response to said optical force probes, said surface deflection which is a function of the viscoelastic response of the at least one object.

49. The method according to claim 48, wherein a comparison of two objects with known optical deformation characteristics under equivalent illumination and optical forcing conditions, compares their viscoelastic responses.

50. The method according to claim 47, further comprising:
controlling a magnitude of the optically generated forces applied to the at least one object using a laser attenuator.

51. The method according to claim 46, further comprising:
directing said diffracted second light beam into said objective lens using a first dichroic mirror; and
directing said first light beam from said first light source to said detector after having passed through said substrate, using a second dichroic mirror.

52. The method according to claim 46, further comprising:
transmitting said first portion of said first light beam which is undiffracted, through the sample containing said at least one object without being diffracted by said at least one object; and
yielding an undiffracted reference beam which later recombines and interferes with said second portion of said first light beam that is diffracted by at least one object, to yield said interference pattern.

53. The method according to claim 52, further comprising:
splitting said first light beam into a reference beam and an object beam using a first beam splitter, said object beam which illuminates said at least one object, and said reference beam which is undiffracted and directed to said detector;
combining said object beam and said reference beam in an off-axis geometry at said detector; and
detecting said interference pattern between said reference beam and said object beam.

54. The method according to claim 53, further comprising:
directing said object beam to said detector using said second dichroic mirror.

55. The method according to claim 54, further comprising:
directing said reference beam from said first beam splitter to said detector using a second beam splitter; and
directing said object beam from said second dichroic mirror to said detector using said second beam splitter.

56. The method according to claim 55, wherein at said detector, said reference beam is temporally coherent with said object beam, such that said interference pattern is generated at said detector; and
wherein a quantitative phase profile of said at least one object is obtained from said interference pattern.

57. The method according to claim 54, further comprising:
disposing a holographic optical element between said second dichroic mirror and said second beam splitter; and
diffracting said object beam into four beamlets and directing said beamlets to said second beam splitter and to said detector, generating four spatially phase-stepped replicas of said object beam.

58. The method according to claim 57, further comprising:
making phase-stepped replicas of images of said at least one object using said holographic optical element, which are diffracted into four quadrants of said detector and simultaneously interfered with said reference beam.

59. The method according to claim 58, further comprising:
computing a phase profile of said at least one object from said four holographically phase-stepped replica images interfered with said reference beam.

60. The method according to claim 58, further comprising:
disposing a transfer lens between said holographic optical element and said second beam splitter.

61. The method according to claim 46, further comprising:
disposing at least one bead on a surface of the at least one object; and
applying said optically generated force to said at least one bead, such that optical forces are applied to said bead;
wherein said optically generated force on said at least one bead exerts pressure on the at least one object underlying said at least one bead to deform the at least one object.

62. The method according to claim 61, further comprising:
determining a three dimensional position of each of said at least one bead by applying Mie theory to an in-line holographic image of said bead, which is an interference pattern between a diffracted beam and an undiffracted beam.

63. The method according to claim 62, further comprising:
determining said position of said bead before and after an application of said optically generated force to measure a deformation displacement on said surface of said at least one object.

64. The method according to claim 63, further comprising:
directing said undiffracted and diffracted light beams from said first light source using a mirror, to said detector via said second dichroic mirror.

65. The method according to claim 45, wherein said substrate is included in a microscope, said microscope having an objective lens.

66. The method according to claim 45, wherein said light source is an imaging laser or a superluminescent diode.

67. The apparatus according to claim 66, further comprising:
modifying an image signal from said superluminescent diode using a correcting lens placed at a focal plane of an image generated therefrom.

68. The method according to claim 45, further comprising:
a computer having a program which analyzes said interference pattern.

69. The method according to claim 45, wherein said detector is one of a high-speed or a fast-detector camera.

70. The method according to claim 45, wherein said laser is a continuous wave or pulsed forcing laser.

71. The method according to claim 45, wherein said at least one object is an adherent cell disposed on the substrate.

72. The method according to claim 71, wherein said at least one cell is grown on an amorphous fluorpolymer-coated cover glass.

73. The method according to claim 71, wherein said at least one cell is grown on a cover glass coated with a molecule, including a protein.

74. The method according to claim 71, wherein optical path length of the adherent cell is measured when no optically generated force is present, and measured after an optically generated force is applied, to yield an optical deformability of the adherent cell, which is compared with measurements of carcinoma cells to determine whether the adherent cell is cancerous.

75. The method according to claim 74, wherein carcinoma cells express a cytoskeletal protein including vimentin, and wherein said cytoskeletal protein mediated change in cellular deformability is used as a diagnostic marker.

76. The method according to claim 45, wherein a measurement of a phase distribution before and after optical forcing of said at least one object, provides an optical path-length shift determination which denotes an optical deformability of said at least one object.

77. The method according to claim 45, further comprising:
moving said sample to a location of said second light beam of said optical forcing mechanism.

78. The method according to claim 77, wherein said sample is moved using a movable sample stage wherein said light beam is moved by movable mirrors and acousto-optic modulators.

79. The method according to claim 78, wherein said sample stage is temperature-controlled.

80. The apparatus according to claim 45, further comprising:
correlating measurements of optical deformability with measurements of cytoskeletal protein expression and with measurements of invasiveness, to determine whether carcinomas are present.

81. The method according to claim 45, further comprising:
illuminating the at least one object on the substrate using a lamp.

82. The method according to claim 81, further comprising:
transmitting a visible band of light to said detector.

83. The method according to claim 82, further comprising:
blocking said first light beam and said second light beam from entering said detector.

84. The method according to claim 45, further comprising:
measuring optical path lengths of the at least one object over a field of view, pixel by pixel, according to spatial light modulated force microscopy techniques.

85. The method according to claim 84, further comprising:
modifying a wavefront from said laser of said holographic optical trapping apparatus, to apply points of light to locations of interest where the at least one object is present in said field of view.

86. The method according to claim 45, further comprising:
generating said phase-shifted or diffracted image by stepping a phase of the DC component of the unmodified image through four phase shifts, and capturing the resultant four images, which store an interference of same, pixel by pixel, and obtaining a phase difference between them.

* * * * *